US011147791B2

(12) United States Patent
Tamura et al.

(10) Patent No.: US 11,147,791 B2
(45) Date of Patent: Oct. 19, 2021

(54) COMPOSITION FOR ACTIVATING SYMPATHETIC NERVE

(71) Applicant: Meiji Co., Ltd., Tokyo (JP)

(72) Inventors: Kazuji Tamura, Odawara (JP); Hiroki Ohara, Odawara (JP)

(73) Assignee: Meiji Co., Ltd.

( * ) Notice: Subject to any disclaimer, the term of this patent is extended or adjusted under 35 U.S.C. 154(b) by 160 days.

(21) Appl. No.: 16/464,365

(22) PCT Filed: Nov. 28, 2017

(86) PCT No.: PCT/JP2017/042507
§ 371 (c)(1),
(2) Date: May 28, 2019

(87) PCT Pub. No.: WO2018/101231
PCT Pub. Date: Jun. 7, 2018

(65) Prior Publication Data
US 2021/0113517 A1 Apr. 22, 2021

(30) Foreign Application Priority Data

Nov. 29, 2016 (JP) .............................. JP2016-231569

(51) Int. Cl.
*A61K 31/353* (2006.01)
*A23L 33/105* (2016.01)
(Continued)

(52) U.S. Cl.
CPC .......... *A61K 31/353* (2013.01); *A23L 33/105* (2016.08); *A61P 25/00* (2018.01); *A61K 9/28* (2013.01)

(58) Field of Classification Search
CPC ...... A61K 31/353; A61K 9/28; A61K 9/0053; A23L 33/105; A61P 25/00; A61P 3/00; A61P 9/00; A61P 25/02
(Continued)

(56) References Cited

U.S. PATENT DOCUMENTS 10,695,317 B2 6/2020 Natsume et al.
2008/0044453 A1 2/2008 Kobayashi et al.

FOREIGN PATENT DOCUMENTS

AU  2016230139 B2 * 9/2016
JP  11308978 A  11/1999
(Continued)

OTHER PUBLICATIONS

Kamio et al., "A single oral dose of flavan-3-ols enhances energy expenditure by sympathetic nerve stimulation in mice", Free Radical Biology and Medicine, 2016, pp. 256-263, vol. 91.
(Continued)

*Primary Examiner* — Taylor V Oh
(74) *Attorney, Agent, or Firm* — The Webb Law Firm

(57) ABSTRACT

An object of the present invention is to provide a novel composition for use in activating a sympathetic nerve. The present invention provides a composition for use in activating a sympathetic nerve, comprising a polyphenol as an active ingredient. The polyphenol comprises 25% by mass or more of monomeric to tetrameric polyphenols, and the monomeric to tetrameric polyphenols include at least catechin, epicatechin, procyanidin B2, procyanidin B5, procyanidin C1 and cinnamtannin A2.

13 Claims, 2 Drawing Sheets

(51) Int. Cl.
*A61P 25/00* (2006.01)
*A61K 9/28* (2006.01)

(58) Field of Classification Search
USPC .................................................... 514/456
See application file for complete search history.

(56) References Cited

FOREIGN PATENT DOCUMENTS

| JP | 2009183229 A | 8/2009 |
| JP | 2012126683 A | 7/2012 |
| JP | 2015221808 A | 12/2015 |
| WO | 2004022049 A1 | 3/2004 |
| WO | 2005030200 A1 | 4/2005 |
| WO | 2016103699 A1 | 6/2016 |
| WO | 2016143745 A1 | 9/2016 |
| WO | 2016181945 A1 | 11/2016 |

OTHER PUBLICATIONS

Matsumura et al., "Enhancement of Energy Expenditure following a Single Oral Dose of Flavan-3-Ols Associated with an Increase in Catecholamine Secretion", PLoS One, 2014, 7 pages, vol. 9, No. 11, Article No. e112180.

Ochi et al., "Development of an Enteric Dry Emulsion Intended for Avoidance of Digestive Metabolism of Epigallocatechin Gallate", The Archives of Practical Pharmacy, 2010, 5 pages, vol. 70, Supplement.

Osakabe et al., "Development of Novel Functionality via Sympathomimetic Effects of Procyanidin", Special Education and Research Reports of Shibaura Institute of Technology, 2016, pp. 233-235, vol. 2015.

Price et al., "Rapid Visual Estimation and Spectrophotometric Determination of Tannin Content of Sorghum Grain", Journal of Agricultural and Food Chemistry, 1977, pp. 1268-1273, vol. 25, No. 6.

Shen et al., "Olfactory stimulation with scent of lavender oil affects autonomic nerves, lipolysis and appetite in rats", Neuroscience Letters, 2005, pp. 188-193, vol. 383.

Tanida et al., "Effects of intraduodenal injection of Lactobacillus johnsonii La1 on renal sympathetic nerve activity and blood pressure in urethane-anesthetized rats", Neuroscience Letters, 2005, pp. 109-114, vol. 389.

Yamashita et al., "Prevention mechanisms of glucose intolerance and obesity by cacao liquor procyanidin extract in high-fat diet-fed C57BL/6 mice", Archives of Biochemisry and Biophysics, 2012, pp. 95-104, vol. 527, No. 2.

* cited by examiner

COMPOSITION FOR ACTIVATING SYMPATHETIC NERVE

CROSS-REFERENCE TO RELATED APPLICATIONS

This application is the U.S. national phase of International Application No. PCT/JP2017/042507 filed Nov. 28, 2017, and claims priority to Japanese Patent Application No. 2016-231569 filed Nov. 29, 2016, the disclosures of which are hereby incorporated by reference in their entirety.

TECHNICAL FIELD

The present invention relates to a composition for use in activating a sympathetic nerve.

BACKGROUND ART

The autonomic nervous system is composed of two systems, i.e., sympathetic nervous system and parasympathetic nervous system, and these two nervous systems exert almost antagonistic effects on organs and tissues, and always regulate circulatory, respiratory, digestive, metabolic, excretory, secretory, thermoregulatory and other functions, which are important for maintenance of living bodies, to maintain homeostasis. Sympathetic nerves are referred to also as nerves for fight and flight, and exhibit various effects such as fat burning, elevation of body temperature, elevation of blood pressure, elevation of blood glucose level, increase in heart rate, and elevation of mental and physical activities. From these effects, it can be expected to activate sympathetic nerves to promote the action of enhancing the systemic vitality.

For example, an agent for activating a sympathetic nerve containing methyl 2-methoxybenzoate has been proposed as the technique for activating a sympathetic nerve (JP 2015-221808 A). Further, an agent for activating a sympathetic nerve comprising orotic acid as an active ingredient has been proposed (JP 2015-126683 A). However, it has never been known so far that polyphenols activate sympathetic nerves.

SUMMARY OF THE INVENTION

An object of the present invention is to provide a novel composition for use in activating a sympathetic nerve and a novel agent for activating a sympathetic nerve.

The present inventors have repeatedly made earnest studies on materials which activate a sympathetic nerve, thereby improving mental and physical activities. As a result, the present inventors have found that intragastric administration and intraduodenal administration of cacao polyphenols can elevate brown adipose tissue sympathetic nerve activity and adrenal gland sympathetic nerve activity. The present invention is based on this finding.

The present invention provides the following inventions.

[1] A composition for use in activating a sympathetic nerve and an agent for activating a sympathetic nerve (hereinafter sometimes referred to as "the composition and agent according to the present invention"), each comprising a polyphenol as an active ingredient.

[2] The composition and agent according to [1], wherein the polyphenol is a cacao polyphenol.

[3] The composition and agent according to [2], wherein the cacao polyphenol comprises 25% by mass or more of monomeric to tetrameric polyphenols.

[4] The composition and agent according to [3], wherein the monomeric to tetrameric polyphenols include at least catechin, epicatechin, procyanidin B2, procyanidin B5, procyanidin C1 and cinnamtannin A2.

[5] The composition and agent according to any one of [1] to [4], which are each substantially free of theobromine.

[6] The composition and agent according to any one of [1] to [5], which are each substantially free of caffeine.

[7] The composition and agent according to any one of [1] to [6], wherein the sympathetic nerve is either or both of brown adipose sympathetic nerve and adrenal gland sympathetic nerve.

[8] The composition and agent according to any one of [1] to [7], which each comprise an intake of the polyphenol effective to activate the sympathetic nerve.

[9] The composition and agent according to [8], wherein the intake of the polyphenol effective to activate the sympathetic nerve is 20 to 2000 mg daily for adults in terms of the total polyphenol amount.

[10] The composition and agent according to any one of [1] to [9], which are each in the form of a unit package.

[11] The composition and agent according to any one of [1] to [10], which are each in the form of an enteric preparation.

[12] The composition and agent according to any one of [1] to [11], which are each a food composition.

[13] A method for activating a sympathetic nerve, comprising feeding or administering an effective amount of a polyphenol to a mammal.

[14] Use of a polyphenol for the manufacture of an agent for activating a sympathetic nerve or as an agent for activating a sympathetic nerve.

[15] A polyphenol for use in activating a sympathetic nerve.

The present invention provides a composition for use in activating a sympathetic nerve and an agent for activating a sympathetic nerve, each comprising a polyphenol as an active ingredient. Polyphenols are contained in various raw materials for foods such as cacao beans, and such polyphenol-containing raw materials have been used as raw materials for foods for a long time. The composition and agent according to the present invention utilize a polyphenol as an active ingredient, and thus are advantageous in having no fear of side effects, even when continuously taken over a long term, and having high safety.

DETAILED DESCRIPTION OF THE INVENTION

Figure 1:
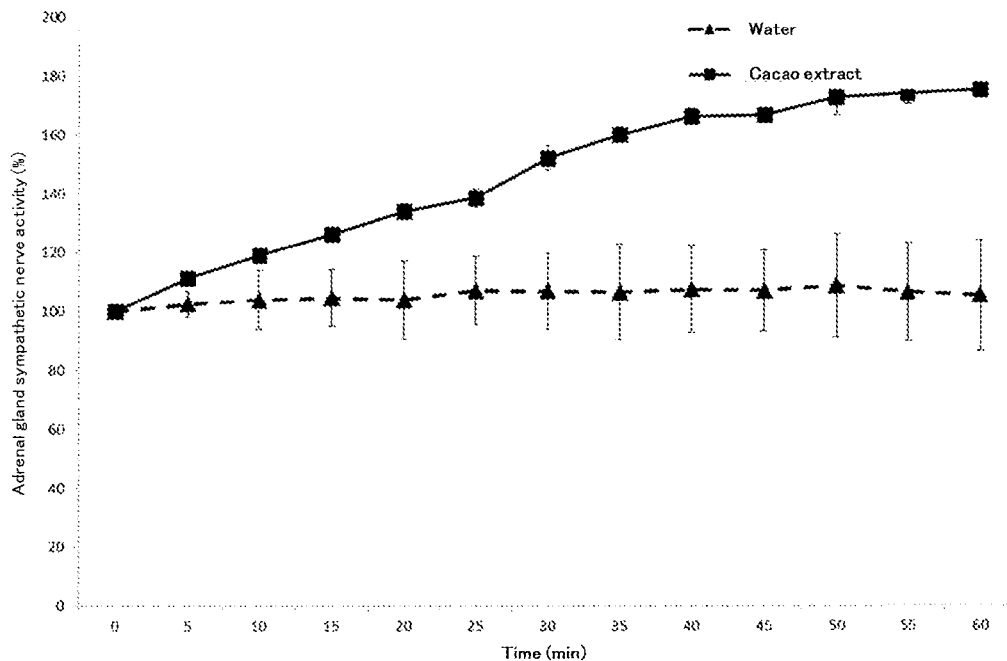
FIG. 1 shows a change in adrenal gland sympathetic nerve activity with time at the time of intragastric administration of cacao polyphenols.

The "polyphenol" which is the active ingredient of the composition and agent according to the present invention is a compound having a structure in which two or more hydroxyl groups are attached to a benzene ring. Polyphenols are classified into simple phenols, flavonoids, hydrolyzable tannins and condensed tannins (proanthocyanidins).

In the present invention, in addition to synthetic products, polyphenols derived from natural products can be utilized as the polyphenol, and, for example, polyphenols derived from cacao beans, tea leaves, grape, lemon, coffee, purple sweet potatoes, and soybeans can be utilized. Squeezed juices of fruits, vegetables, seeds and plant bodies containing a lot of these polyphenols, or extracts thereof, or processed products thereof can be blended as the polyphenol in the composition and agent according to the present invention.

In the present invention, the polyphenol can be a cacao polyphenol. The term "cacao polyphenol" means a polyphenol contained in cacao, i.e., a cacao-derived polyphenol. Accordingly, a polyphenol of cacao extracted (including rough extraction) or purified (including rough purification) from a plant body of cacao or a processed product thereof can be used as the active ingredient of the present invention. Alternatively, part or all of polyphenols prepared by a chemical synthesis method may be used as cacao polyphenol. Examples of the cacao polyphenol include monomers such as catechin, epicatechin and clovamide and oligomers (dimers and higher oligomers) such as procyanidin and tannin formed by polymerization of catechin and the like.

In the present invention, examples of the plant body of cacao or processed product thereof, which can be used as a raw material of cacao polyphenols, can include various sites of the plant body or processed products of cacao beans, such as cacao bark, cacao leaves, cacao beans, cacao shell, cacao mass, defatted cacao mass and cocoa powder. Cacao mass is obtained by grinding cacao beans, and defatted cacao mass can be obtained by removing oil and fat from cacao mass. The method for removing oil and fat is not particularly limited, and oil and fat can be removed according to a known method such as squeezing. Crushing of defatted cacao mass produces cocoa powder. Also, when the plant body of cacao or processed product thereof is used as a raw material for extraction, cacao mass or cocoa powder, which has been subjected to pulverization treatment such as grinding or crushing, is preferably used from the viewpoint of extraction efficiency. The plant body of cacao can include materials other than the plant body of cacao, with or without intention. Also when the plant body of cacao or processed product thereof is used as a raw material for extraction, the plant body of cacao or processed product thereof can include materials other than the plant body of cacao, with or without intention. Further, the cacao mass and cocoa powder can also include materials other than the plant body of cacao, with or without intention.

An extraction method using a plant body of cacao or a processed product thereof as a raw material is known, and a cacao polyphenol-containing composition can be prepared according to the description of JP 2009-183229 A, JP 2011-93807 A, or the like. An extraction solvent is not particularly limited, but water or an alcohol such as ethanol is preferably used. As a purification method using a plant body of cacao or a processed product thereof as a raw material, a known method such as a synthetic adsorbent, an ion exchange resin, ultrafiltration or activated clay treatment can be used without any particular limitation.

In the present invention, the polyphenols can contain monomeric to tetrameric polyphenols in an amount of 25% by mass or more, preferably 40% by mass or more, more preferably 50% by mass or more based on the total amount of polyphenols (hereinafter referred to as "total polyphenol amount" in some cases), and the polyphenols can contain, for example, in an amount of 25% to 70% by mass, preferably 40% to 70% by mass, more preferably 50% to 70% by mass.

In the present invention, the polyphenols can contain 6 kinds of polyphenols, i.e., catechin, epicatechin, procyanidin B2, procyanidin B5, procyanidin C1 and cinnamtannin A2, in an amount of 20% by mass or more, preferably 30% by mass or more, more preferably 40% by mass or more based on the total polyphenol amount, and the polyphenols can contain them, for example, in an amount of 20% to 60% by mass, preferably 30% to 60% by mass, more preferably 40% to 60% by mass.

The polyphenol content in the present invention can be measured by a Prussian blue method. For example, the polyphenol content can be calculated using a commercial epicatechin as a standard substance according to the method described in Martin L. Price and Larry G. Butler, J. Agric Food Chem., Vol. 25, No. 6, 1268-1273, 1977. Also, the contents of the respective ingredients of the polyphenol can be measured using a commercial epicatechin as a standard substance by high-performance liquid chromatography (HPLC).

For effectively administering or feeding a polyphenol, a composition comprising a concentrated polyphenol is preferably used in the present invention. In this case, a polyphenol-concentrated composition obtained according to a known method (for example, the method described in JP 2009-183229 A) can be used in the present invention.

Since cacao polyphenols, among polyphenols, can be prepared using a plant body of cacao as a raw material, the composition and agent according to the present invention each containing a cacao polyphenol as an active ingredient may comprise an ingredient derived from cacao beans, other than the cacao polyphenol. Examples of such an ingredient include theobromine, caffeine, proteins, peptides, amino acids, saccharides, carbohydrates, lipids, dietary fibers, and minerals. It should be noted that theobromine is known to have a physiological effect of causing headache and the like, and that caffeine is known to have a physiological effect of causing insomnia, nausea, headache (in habitual use) and the like. Thus, the composition and agent according to the present invention can be designed so as to be substantially free of either or both of theobromine and caffeine. In such a composition and an agent, the content of theobromine and caffeine can be adjusted to be not higher than the minimum limit of quantification, preferably to be not higher than the limit of detection. The composition and agent according to the present invention which are substantially free of either or both of theobromine and caffeine are advantageous in that they can activate a sympathetic nerve while avoiding the effect of causing headache, nausea and the like.

Polyphenols have a sympathetic nerve activating effect, as will be described in the following Example. Accordingly, polyphenols can be used as an active ingredient of a composition for use in activating a sympathetic nerve, and can also be used as an active ingredient of a method for activating a sympathetic nerve. Also, polyphenols can be used as an active ingredient of an agent for activating a sympathetic nerve.

That is, the present invention provides a method for activating a sympathetic nerve comprising feeding or administering an effective amount of a polyphenol to a human or a non-human animal (for example, a non-human mammal). The method of the present invention can be carried out by administering an effective amount of a polyphenol to mammals including a human in need thereof.

The present invention also provides use of a polyphenol for the manufacture of a composition and a food for use in activating a sympathetic nerve. The present invention further provides use of a polyphenol for the manufacture of an agent for activating a sympathetic nerve. The present invention further provides a polyphenol for use in activating a sympathetic nerve.

In the present invention, the phrase "activating a sympathetic nerve" means activating the activities of sympathetic nerves controlling organs and tissues such as adrenal glands, brown adipose, liver, pancreas, and kidney. In a preferred embodiment of the present invention, the sympathetic nerve to be activated can be either or both of brown adipose sympathetic nerve and adrenal gland sympathetic nerve.

The degree of "activating a sympathetic nerve" in the present invention can be evaluated using the electrical activity of a sympathetic nerve as an index (see Example 1). Specifically, it can be decided that the sympathetic nerve has been activated when the neuronal firing frequency after feeding or administration of a polyphenol (preferably 30 minutes after feeding or administration) is beyond the neuronal firing frequency before feeding or administration, preferably about 1.1 times or more, more preferably about 1.2 times or more, further preferably 1.3 times or more, especially preferably 1.4 times or more.

The use of a polyphenol in the present invention may be use in a human and a non-human animal, and is intended to involve both of therapeutic use and non-therapeutic use. The term "non-therapeutic" means elimination of operating, treating or diagnosing activities to a human (i.e., medical activities to a human), and specifically means elimination of a method of performing operation or treatment of, or diagnosis involving, a human by a doctor or a person who receives an instruction from the doctor.

As will be described in the following Example, polyphenols have a sympathetic nerve activating effect and activate the brown adipose sympathetic nerve activity among the sympathetic nerve activities, thereby making it possible to cause physiological effects such as fat burning, promotion of heat production, elevation of body temperature, and elevation of mental and physical activities in a living body. Briefly, upon feeding or administration of a polyphenol to a living body, it is possible to activate the brown adipose sympathetic nerve activity so that physiological activities as described above can be expected, and also to improve and prevent obesity. The activation of the adrenal gland sympathetic nerve activity, among the sympathetic nerve activities, can promote the secretion of adrenalin and cause, for example, homeostasis of physiological effects of elevating blood pressure, elevating blood glucose level, awakening, elevating mental and physical activities, etc., in a living body. In other words, upon feeding or administration of a polyphenol to a living body, it is possible to activate the adrenal gland sympathetic nerve activity so that physiological activities as described above can be expected, also to alleviate sleepiness and to enhance attentiveness and concentration power. Accordingly, the composition and agent according to the present invention can be fed or administered to a living body for the purpose of the physiological effects described above.

The composition and agent according to the present invention can be provided in the form of medicaments, quasi-drugs, foods or beverages, feeds, or the like, and can be implemented according to the following descriptions. The method for activating a sympathetic nerve according to the present invention can be implemented according to the following descriptions.

The polyphenol(s) which are the active ingredient of the present invention can be orally administered to a human and a non-human animal. Examples of oral agents include granules, powders, tablets (including sugar-coated tablets), pills, capsules, syrups, emulsions, and suspensions. These preparations can be made, by a technique normally carried out in the art, using a pharmacologically acceptable carrier. Examples of the pharmacologically acceptable carrier include excipients, binders, diluents, additives, perfumes, buffers, thickeners, colorants, stabilizers, emulsifiers, dispersants, suspending agents, and preservatives. In the present invention, the oral agent may be provided as an enteric preparation so that it would not dissolve in the stomach and would dissolve in the intestines, and, for example, can be provided as a capsule or a tablet whose surface is coated with an enteric film.

The polyphenol(s) which are the active ingredient of the present invention can be administered to a human and a non-human animal in a manner other than oral administration, such as tubal administration, nasal tubal administration, drip infusion or suppository, in accordance with the forms of the composition and agent according to the present invention. For example, the composition and agent according to the present invention are prepared as viscous liquid compositions which comprise a polyphenol or semi-solid compositions which comprise a polyphenol, and thus can be administered even to a human and a non-human animal having deteriorated chewing and swallowing functions so that they cannot be orally fed or administered. The composition and agent according to the present invention are fed or administered in a manner other than oral feeding, whereby the sympathetic nerves of the human and non-human animal can be expected to be activated even when their chewing and swallowing functions are deteriorated due to aging or the like.

The polyphenol(s) which are the active ingredient of the present invention can be orally fed to a human and a non-human animal. When the polyphenol(s) are orally fed, it may be either in an isolated, purified or roughly-purified form or in the form of a food or food raw material comprising the polyphenol(s). Also, when the polyphenol(s) are orally fed to a human and a non-human animal, its state can be arbitrarily selected from an ordinary temperature state, a warm state, a cold state and the like.

When the polyphenol(s) which are the active ingredient of the present invention is provided as a food, the polyphenol(s) can be contained, as it is, in a food, and the food is a food containing an effective amount of the polyphenol(s). The phrase "containing an effective amount" of the polyphenol(s) refers to a content of the polyphenol(s) in an individual food when eaten in a usual amount, which ensures feeding of the polyphenol(s) in an amount within a range as will be described later. The meaning of the term "food" as used herein includes health foods, functional foods, functional health foods (e.g., designated health foods, functional nutritional foods, and foods with function claims), and special purpose foods (e.g., foods for toddlers, foods for expectant and nursing mothers, and foods for diseased persons). The form of the "food" is not particularly limited, and the food may be provided in a beverage form, in a semi-liquid or gelled form, or in a solid form.

The polyphenols have a sympathetic nerve activating effect, and thus can be provided in a state of being contained in a routinely-eaten food or a food taken as a supplement. The form and shape of the food to be provided in the present invention are not particularly limited, and the food may include, for example, foods comprising cacao beans as the main raw material, which are preferably oil-and-fat-processed compositions, more preferably chocolate and cocoa.

A concentrated polyphenol composition can be used in the present invention for effective feeding of the polyphenol(s), as described above. Therefore, the food and supplement comprising cacao beans as the main raw material are preferably those comprising a high concentration of a cacao polyphenol, more preferably oil-and-fat-processed compositions comprising a high concentration of a cacao polyphenol, still more preferably chocolate and cocoa comprising a high concentration of a cacao polyphenol.

The content of the polyphenol(s) in the food and supplement is not particularly limited so long as the polyphenol(s) can be fed. When a cacao polyphenol is blended as the polyphenol, the content thereof in an oil-and-fat-processed composition can be set to, for example, 1% to 10% by mass, and is preferably 1.2% to 8% by mass, more preferably 1.4% to 6% by mass, still more preferably 1.6% to 4% by mass, further preferably 1.8% to 3.5% by mass, especially preferably 2% to 3.4% by mass, per solid content of the composition, from the viewpoint of effective feeding of a cacao polyphenol.

The food to be provided in the present invention is not particularly limited so long as the polyphenol(s) can be contained therein, including foods comprising cacao beans as the main raw material such as chocolate and cocoa, of course. Examples of the food include starch-based foods such as bread, biscuits, noodles, crackers and nutrition supply bars; various confectioneries such as candies, gums, gummi and snacks; milk and dairy products such as cow milk, processed milk, ice creams, fermented milk (yogurt), milk beverages, cheese, butter and cream; desserts such as puddings, jellies, Bavarian cream and mousse; beverages such as non-alcoholic drinks and alcoholic drinks; livestock-meat processed products such as ham and sausages; fish meat processed products such as kamaboko (boiled fish paste), chikuwa (tube-shaped fish paste cake) and fish meat sausages; fruit processed products such as jam and puree; and seasonings such as roux and sauces. The polyphenol(s) can be appropriately blended at an appropriate stage of the manufacture process according to the properties of the respective foods and the intended purpose.

The medicament and food of the present invention utilize polyphenols contained in various foods and food raw materials, and thus can be safely applied to mammals (for example, humans, mice, rats, rabbits, dogs, cats, cows, horses, pigs and monkeys) in need thereof. The dose or intake of the polyphenols can be determined depending, for example, on the sex, age, body weight and symptoms of a recipient, administration period, dosage form, administration route and drug to be combined. When polyphenols are fed as a food, the polyphenols can be fed, for example, so that the total polyphenol amount falls within the range of from 20 to 2000 mg, preferably from 50 to 1000 mg, more preferably from 75 to 750 mg daily for adults. When the polyphenols are fed as a food, the polyphenols can also be fed, for example, so that the content of monomeric to tetrameric polyphenols falls within a range of from 6 to 600 mg, preferably from 15 to 450 mg, more preferably from 25 to 250 mg daily for adults. When the polyphenols are fed as a food, the polyphenols can be fed, for example, so that the content of 6 kinds of polyphenols, i.e., catechin, epicatechin, procyanidin B2, procyanidin B5, procyanidin C1 and cinnamtannin A2 (hereinafter referred to merely as "6 kinds of polyphenols" in some cases) falls within the range of from 5 to 500 mg, preferably from 10 to 400 mg, more preferably from 20 to 200 mg daily for adults.

The composition and agent according to the present invention may be used in combination with any other composition which can be fed orally, without any limitation. For example, limonene is known as an aroma ingredient having a sympathetic nerve activating effect, and the composition and agent according to the present invention are used in combination with one or more selected from lemon and grape fruit containing limonene and processed products thereof, perfumes containing limonene, and the like, thereby making it possible to further enhance the sympathetic nerve activating effect.

The composition and agent according to the present invention can be provided as compositions comprising an intake of the polyphenol(s) effective to activate a sympathetic nerve. In this case, the composition and agent according to the present invention may be packaged so as to ensure feeding of an effective intake of the polyphenol(s), and the package form may be either one package or a plurality of packages so long as the effective intake thereof can be fed.

When the composition and agent according to the present invention are each provided in a package form, it is desirable to give an indication regarding the intake on the package in order to ensure feeding of an effective intake thereof, or to provide a document which gives the indication together. When an effective daily intake is provided in a plurality of packages, it is also possible to provide a plurality of packages containing the effective daily intake as a set, for convenience of feeding.

The composition and agent according to the present invention are each provided in a package form, they can be provided in a unit package form from the viewpoint of convenience of feeding, and are preferably provided in a unit package form per meal. Here, the "unit package form per meal" is a form in which an intake per meal is predetermined, and, for example, food and beverage products which ensure oral feeding of a specific amount include forms of not only common foods, but also beverages (including drink agents), health supplements, functional health foods and supplements.

The intake per meal predetermined in the unit package form may be either the effective daily intake or an intake obtained by dividing the effective daily intake into two or more (preferably two or three) portions. Thus, the unit package form can contain the polyphenols in the daily intake for adults described above based on any of the total polyphenol amount, the content of monomeric to tetrameric polyphenols, and the content of 6 kinds of polyphenols, or can contain the polyphenols in an amount half or one third of the daily intake for adults described above based on any of the total polyphenol amount, the content of monomeric to tetrameric polyphenols, and the content of 6 kinds of polyphenols.

When the composition and agent according to the present invention are each provided in the unit package form, the polyphenols can be blended in the unit dose form so that the total polyphenol amount falls within the range of from 7 to 2000 mg, preferably from 17 to 1000 mg, more preferably from 25 to 750 mg. Specifically, when the daily intake for adults is blended in the unit package form, the polyphenols can be blended in the unit dose form so that the total polyphenol amount falls within the range of from 20 to 2000 mg, preferably from 50 to 1000 mg, more preferably from 75 to 750 mg. When the polyphenols are blended in an amount half of the daily intake for adults in the unit package form, the polyphenols can be blended in the unit dose form so that the total polyphenol amount falls within the range of from 10 to 1000 mg, preferably from 25 to 500 mg, more preferably from 38 to 380 mg. When the polyphenols are blended in an amount one third of the daily intake for adults in the unit package form, the polyphenols can be blended in the unit dose form so that the total polyphenol amount falls within the range of from 7 to 670 mg, preferably from 17 to 330 mg, more preferably from 25 to 250 mg.

When the composition and agent according to the present invention are each provided in the unit package form, the polyphenols can be blended in the unit dose form so that the content of monomeric to tetrameric polyphenols falls within the range of from 2 to 600 mg, preferably from 5 to 450 mg, more preferably from 8 to 250 mg. Specifically, when the daily intake for adults is blended in the unit package form, the polyphenols can be blended in the unit dose form so that the content of monomeric to tetrameric polyphenols falls within the range of from 6 to 600 mg, preferably from 15 to 450 mg, more preferably from 25 to 250 mg. When the amount half of the daily intake for adults is blended in the unit package form, the polyphenols can be blended in the unit dose form so that the content of monomeric to tetrameric polyphenols falls within the range of from 3 to 300 mg, preferably from 8 to 230 mg, more preferably from 13 to 130 mg. Further, when the amount one third of the daily intake for adults is blended in the unit package form, the polyphenols can be blended in the unit dose form so that the content of monomeric to tetrameric polyphenols falls within the range of from 2 to 200 mg, preferably from 5 to 150 mg, more preferably from 8 to 80 mg.

When the composition and agent according to the present invention are each provided in the unit package form, the polyphenols can be blended in the unit dose form so that the content of 6 kinds of polyphenols, i.e., catechin, epicatechin, procyanidin B2, procyanidin B5, procyanidin C1 and cinnamtannin A2, falls within the range of from 2 to 500 mg, preferably from 3 to 400 mg, more preferably from 7 to 200 mg. Specifically, when the daily intake for adults is blended in the unit package form, the polyphenols can be blended in the unit package forms so that the content of the 6 kinds of polyphenols falls within the range of from 5 to 500 mg, preferably from 10 to 400 mg, more preferably from 20 to 200 mg. When the amount half of the daily intake for adults is blended in the unit package form, the polyphenols can be blended in the unit dose form so that the content of the 6 kinds of polyphenols falls within the range of from 3 to 250 mg, preferably from 5 to 200 mg, more preferably from 10 to 100 mg. Also, when the amount one third of the daily intake for adults is blended in the unit package form, the polyphenols can be blended in the unit dose form so that the content of the 6 kinds of polyphenols falls within the range of from 2 to 170 mg, preferably from 3 to 130 mg, more preferably from 7 to 70 mg.

The package form for providing the composition and agent according to the present invention is not particularly limited so long as the form defines a certain amount, and examples thereof include wrapping papers, bags, soft bags, paper containers, cans, bottles, capsules, and other containers in which they can be contained.

The composition and agent according to the present invention can exert their effect upon single feeding. For exerting their effect for a longer period, the composition and agent according to the present invention are each preferably administered or fed continuously for 2 weeks or more, and the administration or feeding period is more preferably 2 to 8 weeks, especially preferably 4 to 8 weeks. The term "continuously" means continuation of daily administration or feeding. When the composition and agent according to the present invention are each provided in the package form, packages containing an effective intake for a certain period (for example, 1 week) may be provided as a set, for continuous feeding.

The composition and agent according to the present invention may be attached with an indication that they have a sympathetic nerve activating effect. In this case, the composition and agent according to the present invention may be attached with some or all of the following indications for better understanding of consumers. Needless to say, the meaning of the phrase "activating a sympathetic nerve" as used herein includes the effects described in the following indications:

improving mental activity;

improving physical activity;

burning fat;

suitable for persons who are concerned about visceral fat;

suitable for persons who are concerned about body fat;

maintaining or elevating body temperature;

maintaining or elevating blood pressure;

suitable for persons with hypotension;

maintaining or elevating blood glucose level;

suitable for persons with hypoglycemia;

awakening;

alleviating sleepiness;

enhancing attentiveness; and enhancing concentration power.

EXAMPLES

Hereinafter, the present invention will be described in more detail by way of the Examples. The present invention is not limited to the Examples.

Example 1: Influence of Cacao Polyphenols on Nerve Activity (1) Analysis of Ingredients of Cacao Polyphenols A high-purity HP cacao extract (CBP Lot. 121120 manufactured by INABATA KORYO CO., LTD., hereinafter referred to as "cacao extract") was used as a test substance. The ingredients contained in the cacao extract were measured using HPLC. A column Deverosil-ODS-HG5 (4.6 mm×250 mm, $\varphi=5\mu$, manufactured by NOMURA CHEMICAL CO., LTD.) was used. An eluent was composed of liquid A and liquid B. An aqueous 0.1% trifluoroacetic acid solution was used as liquid A, and a 0.1% trifluoroacetic acid/acetonitrile solution was used as liquid B. The flow rate of the eluent passing through the column was 0.8 mL/min., and the conditions for gradient were that the proportion of liquid B to be contained in the entire eluent was 10% at the time of beginning, 10% at the time of 5 minutes after beginning, 25% at the time of 35 minutes after beginning, 100% at the time of 40 minutes after beginning, and 100% at the time of 45 minutes after beginning. The amount of the sample to be injected was 10 µL, and the ingredients were quantified in epicatechin equivalent using epicatechin as a standard product. Also, the polyphenol content was measured by a Prussian blue method. Specifically, the polyphenol content was calculated using a commercial epicatechin as a standard product according to the method described in Martin L. Price and Larry G. Butler, J. Agric Food Chem., Vol. 25, No. 6, 1268-1273, 1977.

(2) Results

The analysis results are indicated in Table 1.

TABLE 1

Analysis of ingredients of cacao extract

| Ingredient | Content (mg/g) |
| --- | --- |
| Total polyphenols | 792.0 |
| Catechin (monomer) | 8.3 |
| Epicatechin (monomer) | 165.8 |
| Procyanidin B2 (dimer) | 94.1 |
| Procyanidin B5 (dimer) | 13.4 |
| Procyanidin C1 (trimer) | 51.1 |
| Cinnamtannin A2 (tetramer) | 22.8 |
| Total of 6 kinds of polyphenols | 355.5 |

From the results indicated in Table 1, it was confirmed that the test substance cacao extract contained at least 6 kinds of monomeric to tetrameric polyphenols. Also, theobromine was not detected (not higher than the minimum limit of quantification) in the cacao extract, and caffeine was detected in a very small amount (16.2 mg/g) based on the total polyphenol amount and the total amount of the 6 kinds of polyphenols. Also, the content of the monomeric to tetrameric polyphenols contained in the cacao extract was 421.1 mg/g.

(3) Testing Method

Male Wistar rats (about 9 weeks old) having a body weight of about 300 g were acclimated, for 1 week or more, in a thermostatic animal chamber at 24° C. in a light-dark cycle (lighting from 8 a.m. to 20 p.m.) of 12-hour lightness and 12-hour darkness, and then used for testing. The rats were divided into 6 control and test groups (n=5 for each group). On the day of testing, after 3-hour fasting, the rats were anesthetized with urethane, and a cannula for intragastric administration or intraduodenal administration was inserted. An efferent nerve of adrenal gland sympathetic nerve or brown adipose tissue sympathetic nerve was lifted with an electrode, and the electrical activity of the nerve was measured according to the method as described in Shen J, et al., Neurosci. Lett. 383188-193, 2005 and Tanida M, et al., Neurosci. Lett. 389: 109-114, 2005.

A tube was inserted into the trachea in a period from the beginning of operation to the end of measurement to maintain the airway, and a warming device was used to keep the body temperature (rat rectal temperature) at 35.0±0.5° C. After completion of operation, the measurement value became stable, and, thereafter, the cannula was used to administer the test substance into the stomach or duodenum. The test was then started. Specifically, 1 mL of a polyphenols-containing suspension prepared from the cacao extract described in the above (1) so that the total amount of the 6 kinds of polyphenols indicated in Table 1 was 50 mg/kg of body weight was administered to the test groups, and 1 mL of water was administered to the control groups.

The change in nerve activity for 60 minutes after administration of the test substance was measured electrophysiologically. The measurement value of nerve activity was expressed in percentage when the value before administration (0 minute) of the test substance was 100%, and the average value of firing frequency per 5 seconds (pulse/5 s) every 5 minutes after administration of the test substance±standard error was calculated. The assay of statistically significant differences as the groups was made according to the analysis of variance (ANOVA) with repeated measures. This test is based on the approval of ANBAS CORP./Ethics Committee of Animal Experiment.

(4) Results

Figure 2:
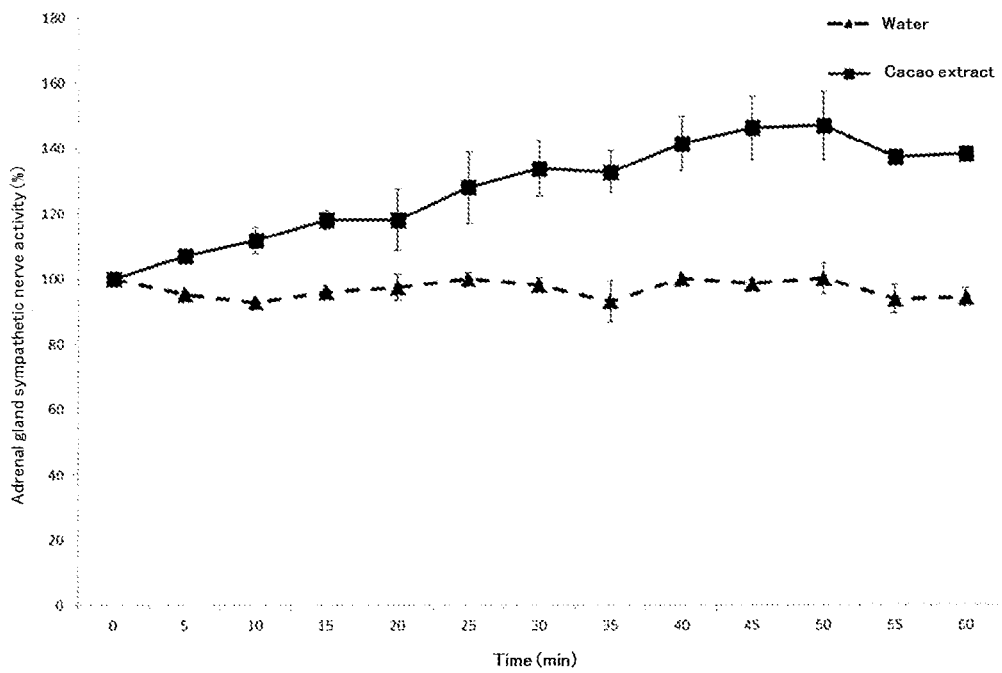
FIG. 2 shows a change in adrenal gland sympathetic nerve activity with time at the time of intraduodenal administration of cacao polyphenols.
Figure 3:
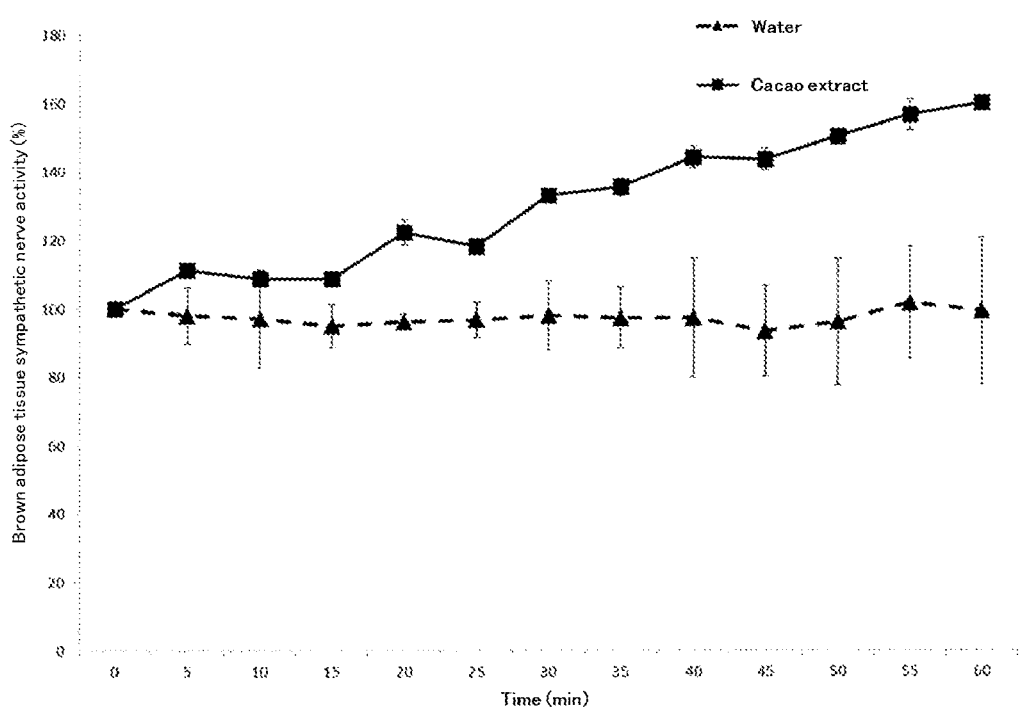
FIG. 3 shows a change in brown adipose tissue sympathetic nerve activity with time at the time of intraduodenal administration of cacao polyphenols.

The results are shown in FIGS. 1 to 3.

From the results shown in FIGS. 1 to 3, it was confirmed that, upon intragastric administration and intraduodenal administration of the cacao extract, the adrenal gland sympathetic nerve activity significantly (P<0.0005, F=107 and P<0.0005, F=86.6, analysis of variance (ANOVA) with repeated measures) enhanced. Also, it was confirmed that, upon intraduodenal administration of the cacao extract, the brown adipose tissue sympathetic nerve activity significantly (P<0.0005, F=93.6, analysis of variance (ANOVA) with repeated measures) enhanced. No statistically significant difference by the Mann-Whitney U test was found between the absolute values of the nerve activities of the test groups and the control groups before administration (0 minute) of the test substance.

The invention claimed is:

1. A method for activating a sympathetic nerve, comprising feeding or administering an effective amount of a polyphenol to a mammal,
wherein the polyphenol is a cacao polyphenol,
wherein the cacao polyphenol is a food composition, and
wherein a firing rate of the sympathetic nerve is increased by 1.4 times or more by the administration of the cacao polyphenol.

2. The method according to claim 1, wherein the cacao polyphenol comprises 25% by mass or more of monomeric to tetrameric polyphenols.

3. The method according to claim 2, wherein the monomeric to tetrameric polyphenols are one or more of catechin, epicatechin, procyanidin B2, procyanidin B5, procyanidin C1 and cinnamtannin A2.

4. The method according to claim 1, wherein the composition is free of theobromine.

5. The method according to claim 1, wherein the composition is free of caffeine.

6. The method according to claim 1, wherein the sympathetic nerve is either or both of brown adipose sympathetic nerve or adrenal gland sympathetic nerve.

7. The method according to claim 1, wherein the effective amount of the polyphenol is 20 to 2000 mg daily for adults in terms of the total polyphenol amount.

8. The method according to claim 1, wherein the food composition is in the form of a unit package.

9. The method according to claim 1, wherein the food composition is in the form of an enteric preparation.

10. The method according to claim 1, wherein the cacao polyphenol comprises 25% by mass or more of monomeric to tetrameric polyphenols, and wherein the monomeric to tetrameric polyphenols are one or more of catechin, epicatechin, procyanidin B2, procyanidin B5, procyanidin C1 and cinnamtannin A2.

11. The method according to claim 10, wherein the sympathetic nerve is either or both of brown adipose sympathetic nerve or adrenal gland sympathetic nerve.

12. The method according to claim 10, wherein the effective amount of the polyphenol is 20 to 2000 mg daily for adults in terms of the total polyphenol amount.

13. The method according to claim 10, wherein the composition is free of theobromine and caffeine, wherein the sympathetic nerve is either or both of brown adipose sympathetic nerve or adrenal gland sympathetic nerve, and wherein the effective amount of the polyphenol is 20 to 2000 mg daily for adults in terms of the total polyphenol amount.

\* \* \* \* \*